United States Patent
Capell et al.

(10) Patent No.: US 10,492,519 B2
(45) Date of Patent: Dec. 3, 2019

(54) CUSTOMIZING NUTRITIONAL SUPPLEMENT SHAKE RECOMMENDATIONS

(71) Applicant: ICON Health & Fitness, Inc., Logan, UT (US)

(72) Inventors: Rebecca Lynn Capell, Logan, UT (US); Megan Jane Ostler, North Logan, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 190 days.

(21) Appl. No.: 15/712,707

(22) Filed: Sep. 22, 2017

(65) Prior Publication Data

US 2018/0084817 A1   Mar. 29, 2018

Related U.S. Application Data (60) Provisional application No. 62/400,780, filed on Sep. 28, 2016.

(51) Int. Cl.
  *G06F 19/00* (2018.01)
  *G16H 20/70* (2018.01)
  (Continued)

(52) U.S. Cl.
  CPC ............ *A23L 33/30* (2016.08); *A61B 5/0002* (2013.01); *G06F 19/32* (2013.01);
  (Continued)

(58) Field of Classification Search
  CPC ..... G16H 20/70; G16H 20/60; G06F 19/3475
  See application file for complete search history.

(56) References Cited

U.S. PATENT DOCUMENTS 5,412,564 A * 5/1995 Ecer .................... G06F 19/3475
                                                600/300
5,954,640 A   9/1999 Szabo
(Continued)

FOREIGN PATENT DOCUMENTS

KR   10-2016-0040699   4/2016
KR   10-2016-0054325   5/2016
(Continued)

OTHER PUBLICATIONS

Sarah, Create Your Own Meal Replacement Shakes DaysToFitness.com, Sep. 24, 2015 (Year: 2015).*

(Continued)

*Primary Examiner* — Scott L Jarrett
(74) *Attorney, Agent, or Firm* — Maschoff Brennan (57) ABSTRACT

A method for customizing nutritional supplement recommendations may include receiving a primary nutritional supplement motivation indication of a user, receiving physical movement data of the user from one or more electronic sensors configured to directly measure physical movement of the user, analyzing the physical movement data, determining one or more physical movement parameters based on the analysis of the physical movement data, generating a custom nutritional supplement recommendation for the user based on the received primary nutritional supplement motivation indication and the determined one or more physical movement parameters.

20 Claims, 10 Drawing Sheets

(51) Int. Cl.
*A23L 33/00* (2016.01)
*A61B 5/00* (2006.01)
*G06Q 10/10* (2012.01)
*G06Q 10/06* (2012.01)

(52) U.S. Cl.
CPC ... *G06Q 10/06311* (2013.01); *G06Q 10/1093* (2013.01); *G16H 20/70* (2018.01)

(56) References Cited

U.S. PATENT DOCUMENTS

| | | | |
|---|---|---|---|
| 7,978,081 B2 | 7/2011 | Shears et al. | |
| 8,326,646 B2* | 12/2012 | Schwarzberg | G06F 19/3475 705/2 |
| 8,446,275 B2* | 5/2013 | Utter, II | A61B 5/0205 340/539.12 |
| 8,504,385 B2* | 8/2013 | Bahar | G06Q 10/10 705/2 |
| 8,626,327 B2* | 1/2014 | Bippert | G06Q 10/06 700/100 |
| 8,684,922 B2* | 4/2014 | Tran | A61B 5/6816 600/300 |
| 8,795,138 B1 | 8/2014 | Yeh et al. | |
| 9,000,933 B2* | 4/2015 | Ray | G08B 21/043 340/627 |
| 9,011,153 B2* | 4/2015 | Bennett | G09B 5/00 434/127 |
| 9,173,517 B2* | 11/2015 | Bulgin | A47J 31/401 |
| 9,183,498 B2* | 11/2015 | Landers | G06N 5/02 |
| 9,468,807 B1* | 10/2016 | Krueger | A63B 24/0075 |
| 9,558,515 B2* | 1/2017 | Babu | G06Q 30/0631 |
| 9,916,612 B2* | 3/2018 | Morris | G06Q 30/0631 |
| 10,108,784 B2* | 10/2018 | Zatvan | G06F 19/00 |
| 10,127,361 B2* | 11/2018 | Hyde | G06F 19/3475 |
| 10,188,230 B2* | 1/2019 | Hambrock | A47G 19/2227 |
| 2003/0069757 A1 | 4/2003 | Greenberg | |
| 2003/0091964 A1* | 5/2003 | Yeager | G06F 19/324 434/127 |
| 2004/0162702 A1 | 8/2004 | Pandipati et al. | |
| 2005/0048461 A1* | 3/2005 | Lahteenmaki | A61J 3/002 435/3 |
| 2005/0113649 A1* | 5/2005 | Bergantino | G06Q 50/22 600/300 |
| 2005/0113650 A1* | 5/2005 | Pacione | A61B 5/411 600/300 |
| 2006/0062859 A1* | 3/2006 | Blum | A61K 31/56 424/725 |
| 2006/0074716 A1* | 4/2006 | Tilles | G06Q 50/22 705/2 |
| 2006/0081653 A1* | 4/2006 | Boland | A47J 31/40 222/243 |
| 2006/0199155 A1* | 9/2006 | Mosher | G09B 19/0092 434/127 |
| 2007/0073557 A1 | 3/2007 | Abramson | |
| 2008/0059225 A1* | 3/2008 | Chang | G06F 19/3418 705/2 |
| 2008/0086318 A1 | 4/2008 | Gilley et al. | |
| 2008/0087352 A1 | 4/2008 | Malanowicz et al. | |
| 2008/0089983 A1* | 4/2008 | Coste | A23G 9/04 426/106 |
| 2008/0162186 A1* | 7/2008 | Jones | G06Q 30/02 705/2 |
| 2008/0177572 A1* | 7/2008 | Fuhrman | G06F 19/3475 705/2 |
| 2009/0055199 A1* | 2/2009 | Yusuf | G06Q 50/12 705/15 |
| 2009/0075242 A1* | 3/2009 | Schwarzberg | G09B 19/0092 434/127 |
| 2009/0148818 A1* | 6/2009 | Li | G09B 19/0092 434/127 |
| 2009/0204473 A1* | 8/2009 | Sommerfeld | G06Q 10/06 705/26.5 |
| 2009/0307007 A1* | 12/2009 | Hermann | G06Q 10/00 705/2 |
| 2010/0040695 A1* | 2/2010 | Feuvrier-Roy | A23P 20/00 424/490 |
| 2010/0280895 A1* | 11/2010 | Mottola | G06F 19/324 705/14.24 |
| 2011/0009708 A1* | 1/2011 | Boyes | G06F 19/3475 600/300 |
| 2011/0014351 A1 | 1/2011 | Reider et al. | |
| 2011/0184247 A1* | 7/2011 | Contant | G06Q 10/10 600/300 |
| 2011/0281249 A1 | 11/2011 | Gammell et al. | |
| 2011/0318717 A1* | 12/2011 | Adamowicz | G16H 20/60 434/127 |
| 2012/0059664 A1* | 3/2012 | Georgiev | A61B 5/02 705/2 |
| 2012/0083669 A1* | 4/2012 | Abujbara | G06F 19/3475 600/300 |
| 2012/0233002 A1* | 9/2012 | Abujbara | G06Q 10/06 705/15 |
| 2012/0285986 A1* | 11/2012 | Irvin | B67D 1/0041 222/1 |
| 2013/0004923 A1* | 1/2013 | Utter, II | G06F 19/3475 434/127 |
| 2013/0095459 A1* | 4/2013 | Tran | A61B 5/6816 434/247 |
| 2013/0158367 A1* | 6/2013 | Pacione | A61B 5/0022 600/301 |
| 2013/0209972 A1 | 8/2013 | Carter et al. | |
| 2013/0253943 A1 | 9/2013 | Lee et al. | |
| 2013/0261183 A1* | 10/2013 | Bhagat | A61K 31/202 514/560 |
| 2013/0268289 A1* | 10/2013 | White-Stein | G16H 15/00 705/2 |
| 2014/0080102 A1 | 3/2014 | Krishna | |
| 2014/0163343 A1 | 6/2014 | Heneghan et al. | |
| 2014/0214446 A1 | 7/2014 | Nusbaum et al. | |
| 2014/0236622 A1* | 8/2014 | Southam | G06Q 30/02 705/2 |
| 2014/0236759 A1* | 8/2014 | Mirabile | G06Q 30/0633 705/26.8 |
| 2014/0287384 A1* | 9/2014 | Boyes | G06F 19/3475 434/127 |
| 2015/0125832 A1* | 5/2015 | Tran | G09B 19/0092 434/127 |
| 2015/0199493 A1* | 7/2015 | Glenn | G06F 19/3418 705/3 |
| 2015/0366405 A1* | 12/2015 | Manchuliantsau | A23L 33/40 222/1 |
| 2016/0004842 A1* | 1/2016 | Landi | G06Q 10/0631 434/262 |
| 2016/0042660 A1* | 2/2016 | Radovcic | G09B 19/0092 434/127 |
| 2016/0055760 A1* | 2/2016 | Mirabile | G16H 10/20 434/236 |
| 2016/0058245 A1 | 3/2016 | Smith et al. | |
| 2017/0098056 A1 | 4/2017 | Reddy et al. | |
| 2017/0193578 A1 | 7/2017 | Watterson | |
| 2018/0352836 A1* | 12/2018 | Cronin | A23L 2/52 |
| 2018/0353002 A1* | 12/2018 | Cronin | A23L 2/52 |

FOREIGN PATENT DOCUMENTS

| | | |
|---|---|---|
| KR | 10-2016-0063126 | 6/2016 |
| WO | 2015021289 | 2/2015 |

OTHER PUBLICATIONS

Create Your Own Formula www.theproteinworks.com/create-your-own, Mar. 19, 2015, Retrieved from Archive.org Jun. 14, 2019 (Year: 2015).*

International Search Report issued for PCT/US2017/053273 dated Dec. 11, 2017.

English Translation of Abstract of KR10-2016-0063126 dated Jun. 3, 2016.

(56) References Cited

OTHER PUBLICATIONS

English Translation of Abstract of KR10-2016-0054325 dated May 16, 2016.
Evolution Nutrition; "Pre- and Post-workout Nutrition for Strength Training"; Webpage; www.acefitness.org/education-and-resources/professional/expert-articles/5390/pre-and-post-workout-nutrition-for-strength-training ; Apr. 23, 2015; 7 pages.
Muth, Natalie Digate; "what can working with a registered dietitian do for me?"; Webpage; www.acefitness.org/education-and-resources/lifestyle/blog/1886/what-can-working-with-a-registered-dietitian-do-for-me ; Oct. 5, 2011; 6 pages.

* cited by examiner

My Preferences

1. Would you like your daily shake to also function as a meal replacement?  ○ Yes  ○ No 2. Which flavor would you like?  ○ Chocolate  ○ Vanilla 3. Do you have any strict dietary restrictions?  [ ▶ ]

CUSTOMIZING NUTRITIONAL SUPPLEMENT SHAKE RECOMMENDATIONS

RELATED APPLICATIONS

This application claims priority to U.S. Patent Application Ser. No. 62/400,780 titled "Customizing Nutritional Supplement Recommendations" and filed on 28 Sep. 2016, which application is herein incorporated by reference for all that it discloses.

BACKGROUND

Nutritional supplements are used by many consumers in an effort to achieve a healthy diet. Many nutritional supplements are intended to provide nutrients that may otherwise not be consumed in sufficient quantities.

Both the demand for and availability of nutritional supplements has increased dramatically in recent years. For example, it is estimated that there are tens of thousands of nutritional supplements for sale in the United States, and it is estimated that over half of the adult population consume nutritional supplements.

One common problem faced by consumers of nutritional supplements is selecting an appropriate nutritional supplement from among the overwhelming number of choices available. One way a consumer may deal with this problem is to consult with a dietitian, who may make a recommendation based on an analysis of the consumer's healthy and unhealthy habits. However, such a consultation can be expensive, time consuming, and subjective, and may also be unhelpful due to the consumer providing subjective and inaccurate information to the dietitian, given that consumers notoriously overestimate their healthy habits and underestimate their unhealthy habits.

SUMMARY

In one aspect of the disclosure, a method for customizing nutritional supplement recommendations may include receiving a primary nutritional supplement motivation indication of a user, receiving physical movement data of the user from one or more electronic sensors configured to directly measure physical movement of the user, analyzing the physical movement data, determining one or more physical movement parameters based on the analysis of the physical movement data, generating a custom nutritional supplement recommendation for the user based on the received primary nutritional supplement motivation indication and the determined one or more physical movement parameters.

Another aspect of the disclosure may include any combination of the above-mentioned features and may further include the one or more electronic sensors including a wearable electronic sensor configured to be worn on a wrist of the user.

Another aspect of the disclosure may include any combination of the above-mentioned features and may further include the determined one or more physical movement parameters including a primary workout of the user.

Another aspect of the disclosure may include any combination of the above-mentioned features and may further include the determined one or more physical movement parameters including a primary activity of the user.

Another aspect of the disclosure may include any combination of the above-mentioned features and may further include the determined one or more physical movement parameters including an average workout time of the user.

Another aspect of the disclosure may include any combination of the above-mentioned features and may further include the method further including receiving the sex of the user and the generating of the custom nutritional supplement recommendation for the user being further based on the received sex of the user.

Another aspect of the disclosure may include any combination of the above-mentioned features and may further include the custom nutritional supplement recommendation including a recommendation to drink a sex-specific nutritional supplement shake.

Another aspect of the disclosure may include any combination of the above-mentioned features and may further include the method further including receiving an allergy status of the user and the generating of the custom nutritional supplement recommendation for the user being further based on the received allergy status of the user.

Another aspect of the disclosure may include any combination of the above-mentioned features and may further include the custom nutritional supplement recommendation including a recommendation to drink a plant-based nutritional supplement shake.

Another aspect of the disclosure may include any combination of the above-mentioned features and may further include the method further including receiving a meal replacement goal of the user and the generating of the custom nutritional supplement recommendation for the user being further based on the received meal replacement goal of the user.

Another aspect of the disclosure may include any combination of the above-mentioned features and may further include the custom nutritional supplement recommendation including a recommendation to drink a meal-replacement nutritional supplement shake.

Another aspect of the disclosure may include any combination of the above-mentioned features and may further include the custom nutritional supplement recommendation including a recommendation to drink a protein nutritional supplement shake.

Another aspect of the disclosure may include any combination of the above-mentioned features and may further include the method further including receiving a weight loss goal of the user and the generating of the custom nutritional supplement recommendation for the user being further based on the received weight loss goal of the user.

Another aspect of the disclosure may include any combination of the above-mentioned features and may further include the custom nutritional supplement recommendation including a recommendation to drink a weight loss nutritional supplement shake.

Another aspect of the disclosure may include any combination of the above-mentioned features and may further include the custom nutritional supplement recommendation including a recommendation to drink a cardio nutritional supplement shake.

Another aspect of the disclosure may include any combination of the above-mentioned features and may further include the custom nutritional supplement recommendation including a recommendation to drink a lean and tone nutritional supplement shake.

Another aspect of the disclosure may include any combination of the above-mentioned features and may further include one or more non-transitory computer-readable media storing one or more programs that are configured, when executed, to cause one or more processors to perform the method for customizing nutritional supplement recommendations.

BRIEF DESCRIPTION OF THE DRAWINGS

The accompanying drawings illustrate various embodiments of the present method and system and are a part of the specification. The illustrated embodiments are merely examples of the present system and method and do not limit the scope thereof.

Throughout the drawings, identical reference numbers designate similar, but not necessarily identical, elements.

DETAILED DESCRIPTION

Methods for customizing nutritional supplement recommendations are disclosed herein. Specifically, the present methods generate custom nutritional supplement recommendations for users based on various data that is received or determined. For example, the received data may include a primary nutritional supplement motivation indication of a user and physical movement data of the user. The received physical movement data may be received from one or more electronic sensors configured to directly measure physical movement of the user. This received physical movement data may then be analyzed and then one or more physical movement parameters may be determined based on the analysis of the physical movement data. Finally, the custom nutritional supplement recommendation for the user may be generated based on the received primary nutritional supplement motivation indication and the determined one or more physical movement parameters. The methods for customizing nutritional supplement recommendations are described in detail below.

Figure 1:
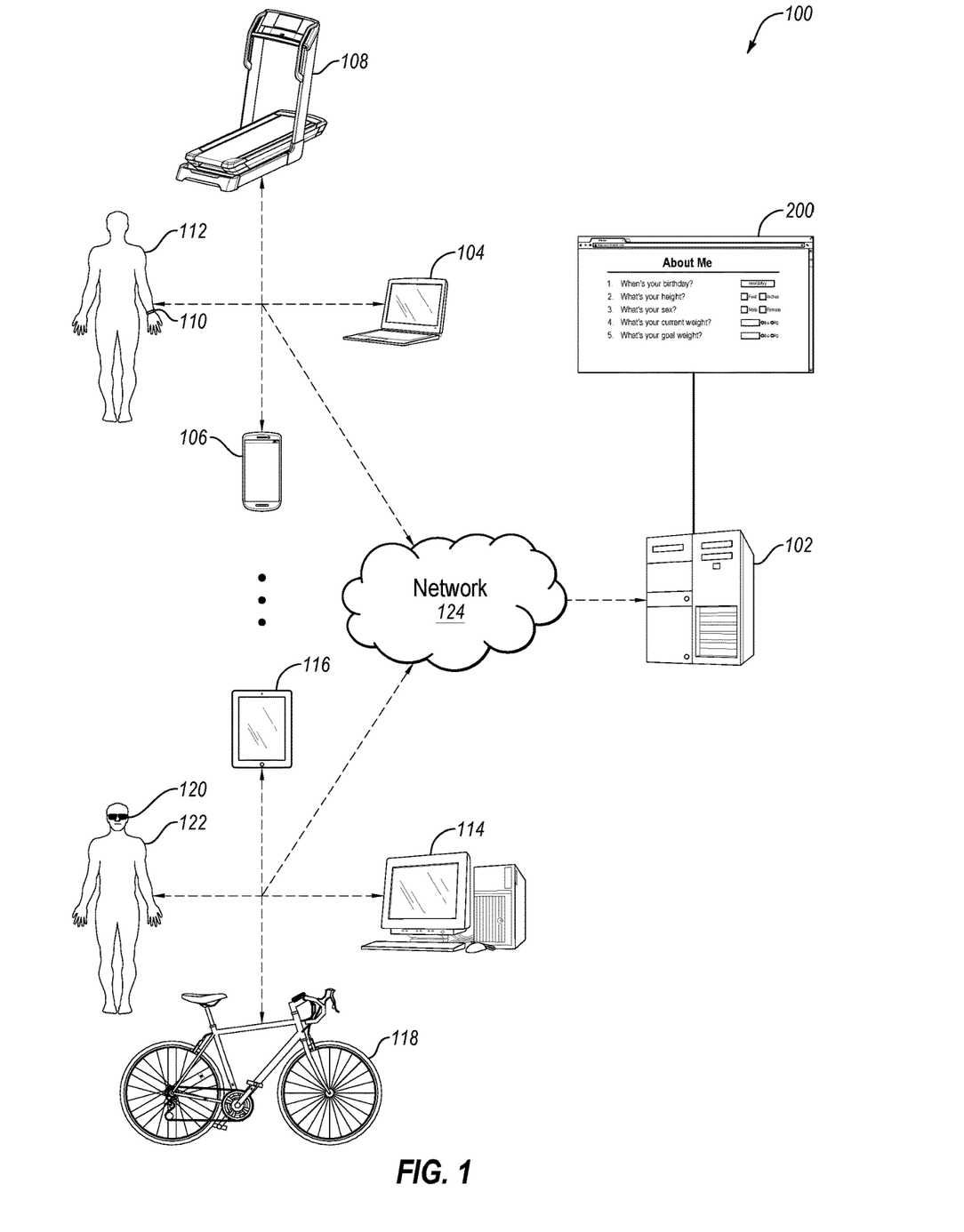
FIG. 1 is a diagram of an example health system.

FIG. 1 is a diagram of an example health system 100. The system 100 may include a server 102 that hosts a website 200. The system 100 may also include a laptop computer 104, a smartphone 106, a treadmill 108, and an activity tracker watch 110 configured to be worn on the wrist of a first user 112. The system 100 may further include a desktop computer 114, a tablet 116, a bicycle 118, and smart glasses 120 configured to be worn by a second user 122.

As disclosed in FIG. 1, each of the computing devices in the system 100 may be configured to communicate with one another wirelessly, either locally or remotely via a network 124. In particular, the activity tracker watch 110 worn by the first user 112 may include an electronic sensor, such as an accelerometer, that is configured to directly measure the physical movement of the first user 112, such as the number of steps taken by the first user 112, resulting in physical movement data. Similarly, the treadmill 108 may include multiple electronic sensors, such as an odometer and a tilt sensor, that are configured to directly measure the physical movement of the first user 112, such as the simulated distance run by the first user 112 on the treadmill 108, and the incline while running, resulting in physical movement data. The physical movement data from the activity tracker watch 110 and the treadmill 108 may be sent to, and received by, the laptop computer 104, the smartphone 106, or the server 102, or some combination thereof. A software application running on the laptop computer 104, the smartphone 106, or the server 102, or some combination thereof, may then be configured to analyze the physical movement data and then determine, based on the analysis of the physical movement data, one or more physical movement parameters. These one or more physical movement parameters may include a primary workout of the first user 112 (such as an aerobic workout, a cardiac workout, or resistance training), a primary activity of the first user 112 (such as walking or typing), or an average workout time of the first user 112 (such as the average number of minutes the first user works out each week), or some combination therefore. After the software application has determined the one or more physical movement parameters, the software application may then generate a custom nutritional supplement recommendation for the first user 112 based at least in part on the one or more physical movement parameters.

Further, the smart glasses 120 worn by the second user 122 may include multiple electronic sensors, such as a GPS receiver and a video camera, that are configured to directly measure the physical movement of the second user 122, such as the distance traveled and the amount of head movement by the second user 122, resulting in physical movement data. Similarly, the bicycle 118 may include an electronic sensor, such as a cadence sensor, that is configured to directly measure the physical movement of the second user 122, such as the number of pedal strokes performed by the second user 122 on the bicycle 118, resulting in physical movement data. The physical movement data from the smart glasses 120 and the bicycle 118 may be sent to, and received by, the desktop computer 114, the tablet 116, or the server 102, or some combination thereof. A software application running on the desktop computer 114, the tablet 116, or the server 102, or some combination thereof, may then be configured to analyze the physical movement data and then determine, based on the analysis of the physical movement data, one or more physical movement parameters. After the software application has determined the one or more physical movement parameters, the software application may then generate a custom nutritional supplement recommendation for the second user 122 based at least in part on the one or more physical movement parameters.

FIGS. 2A-2D are example webpages of the website 200 that may be employed in connection with the system 100 of FIG. 1.

Figure 2A:
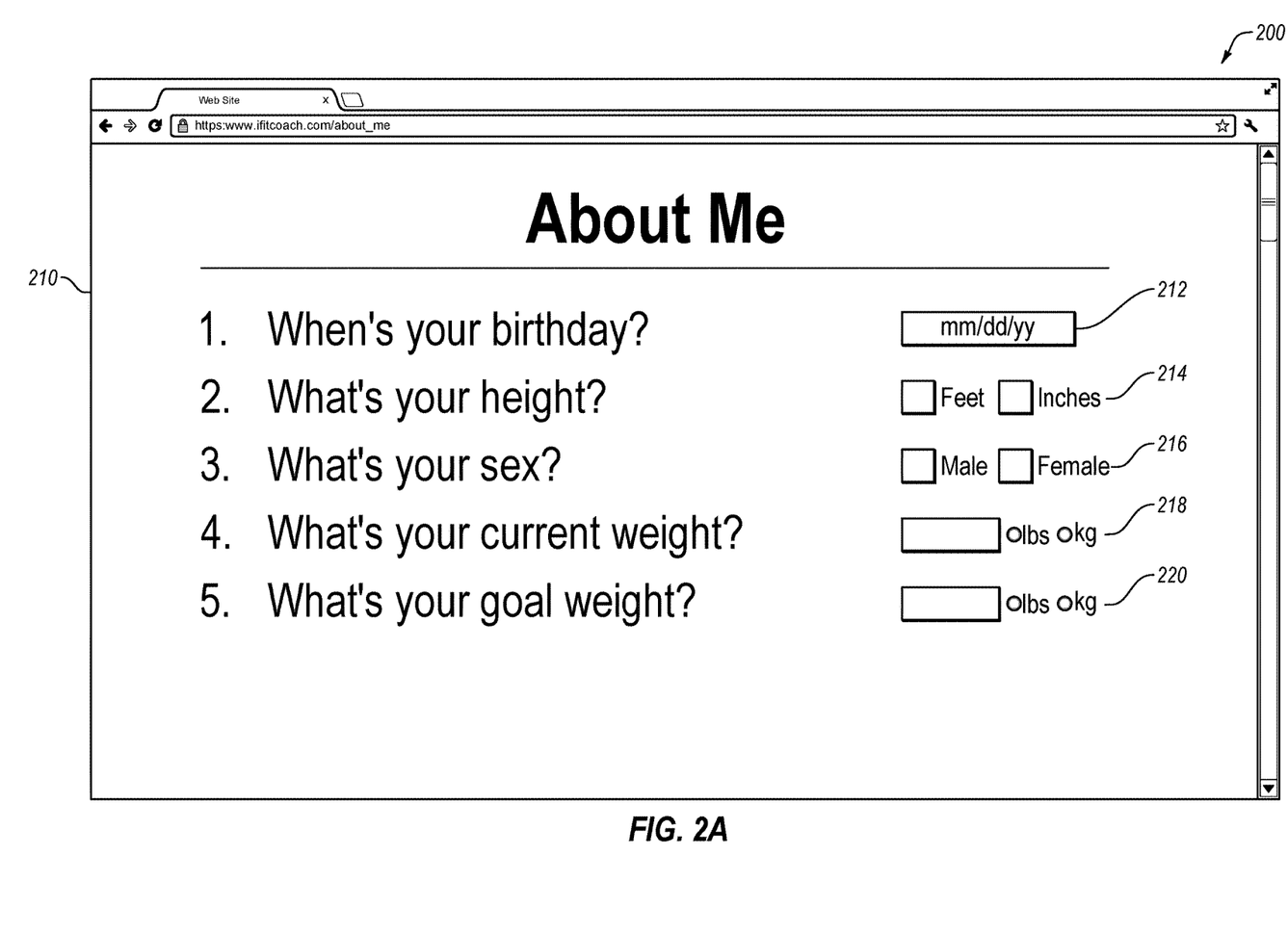
FIGS. 2A-2D are example webpages of an example website that may be employed in connection with the example health system of FIG. 1.

As disclosed in FIG. 2A, a first webpage 210 of the website 200 may be configured to be presented to a user in order to receive data about the user. In particular, the first webpage 210 may be configured to receive the user's birthday, height, sex, current weight, and weight loss goal in data entry fields 212-220, respectively.

Figure 2B:
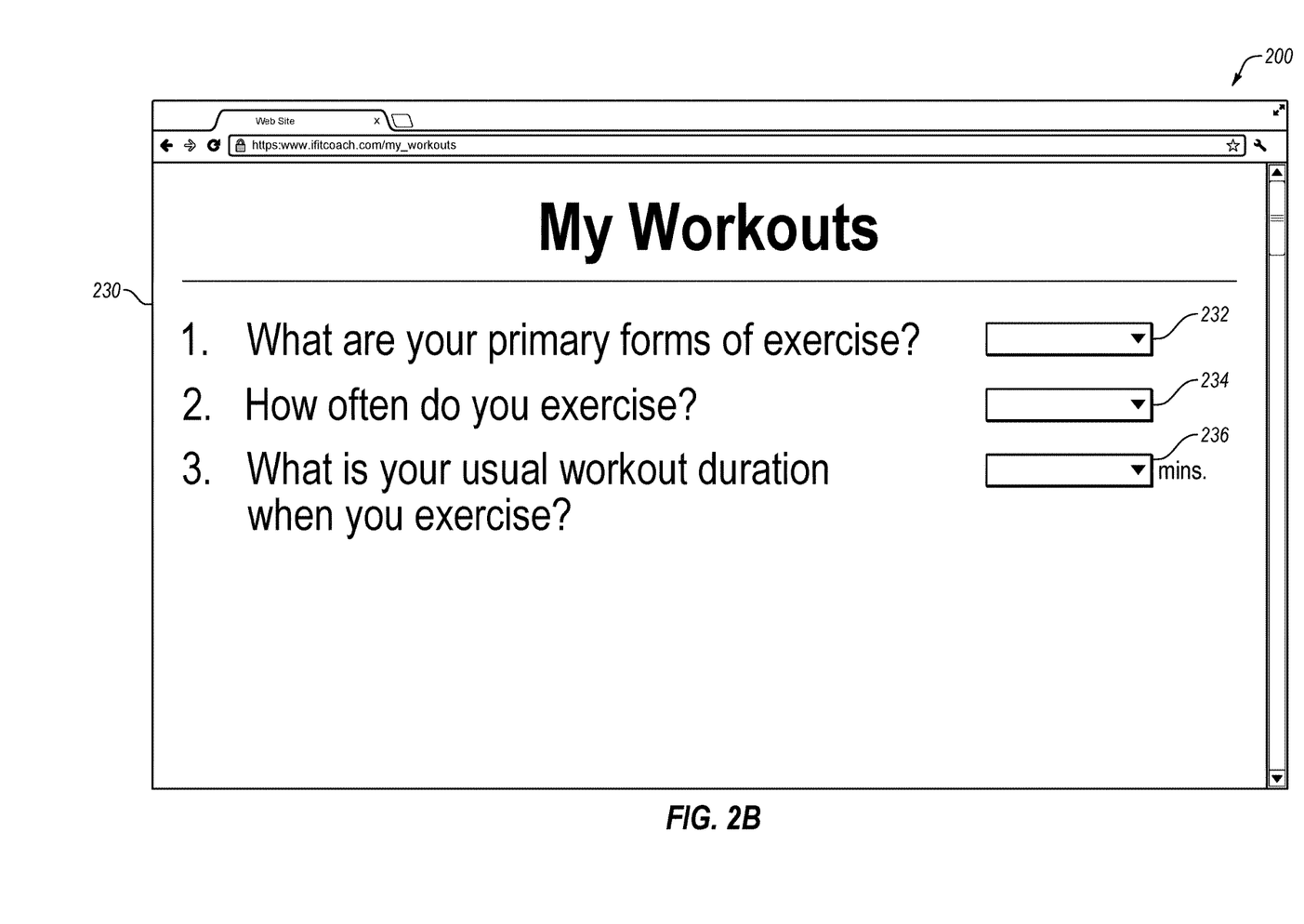

As disclosed in FIG. 2B, a second webpage 230 of the website 200 may be configured to be presented to a user in order to receive data regarding the workouts of the user. In particular, the second webpage 230 may be configured to receive the user's primary workouts, average frequency of working out, and average duration of each workout in data entry fields 232-236, respectively.

Figure 2C:
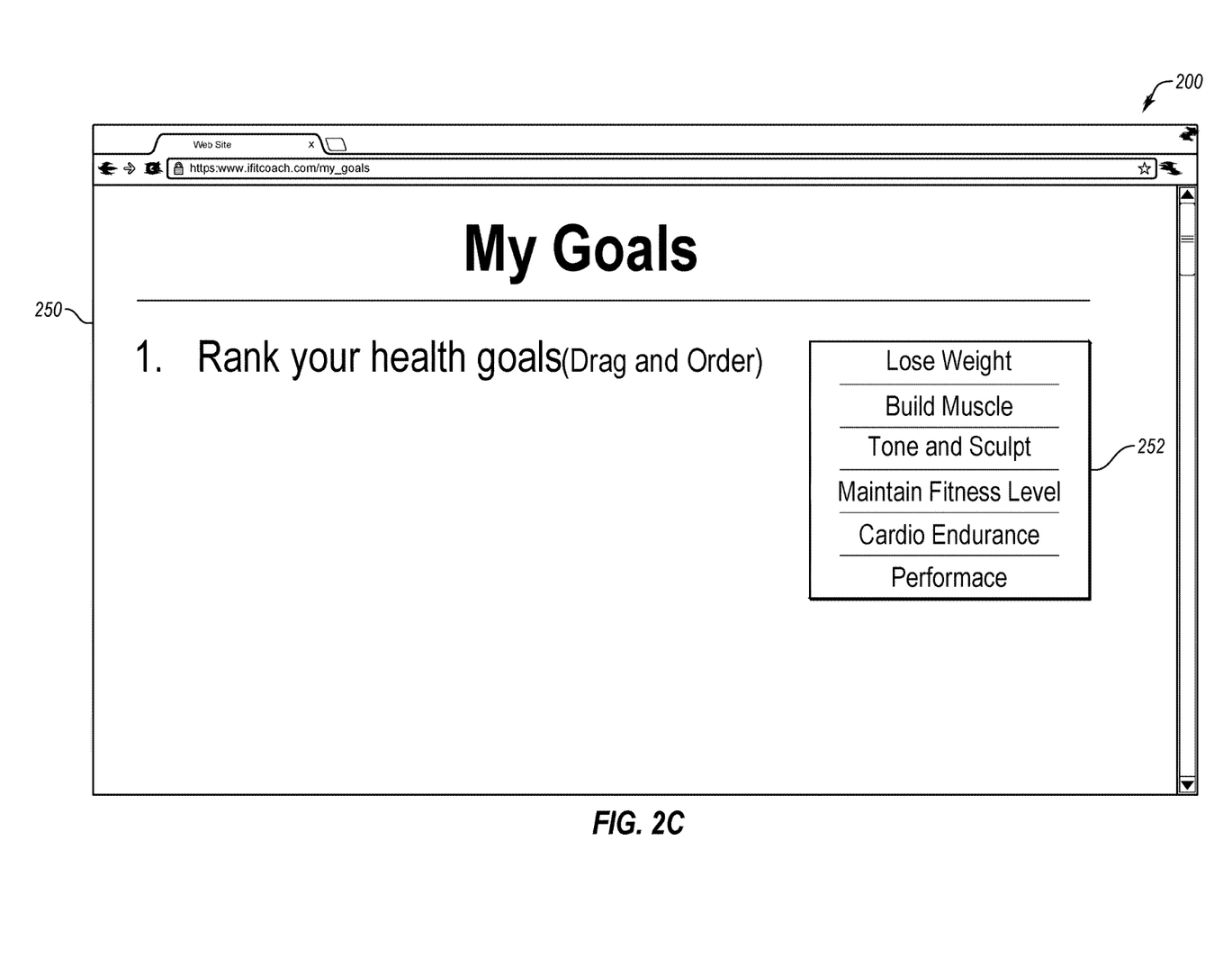

As disclosed in FIG. 2C, a third webpage 250 of the website 200 may be configured to be presented to a user in order to receive data regarding the goals of the user. In particular, the third webpage 250 may be configured to receive a primary nutritional supplement motivation indication from a user by receiving a ranking of the user's health goals in the areas of losing weight, building muscles, toning and sculpting, maintaining a current fitness level, cardio endurance, and performance using data entry fields 252.

Figure 2D:
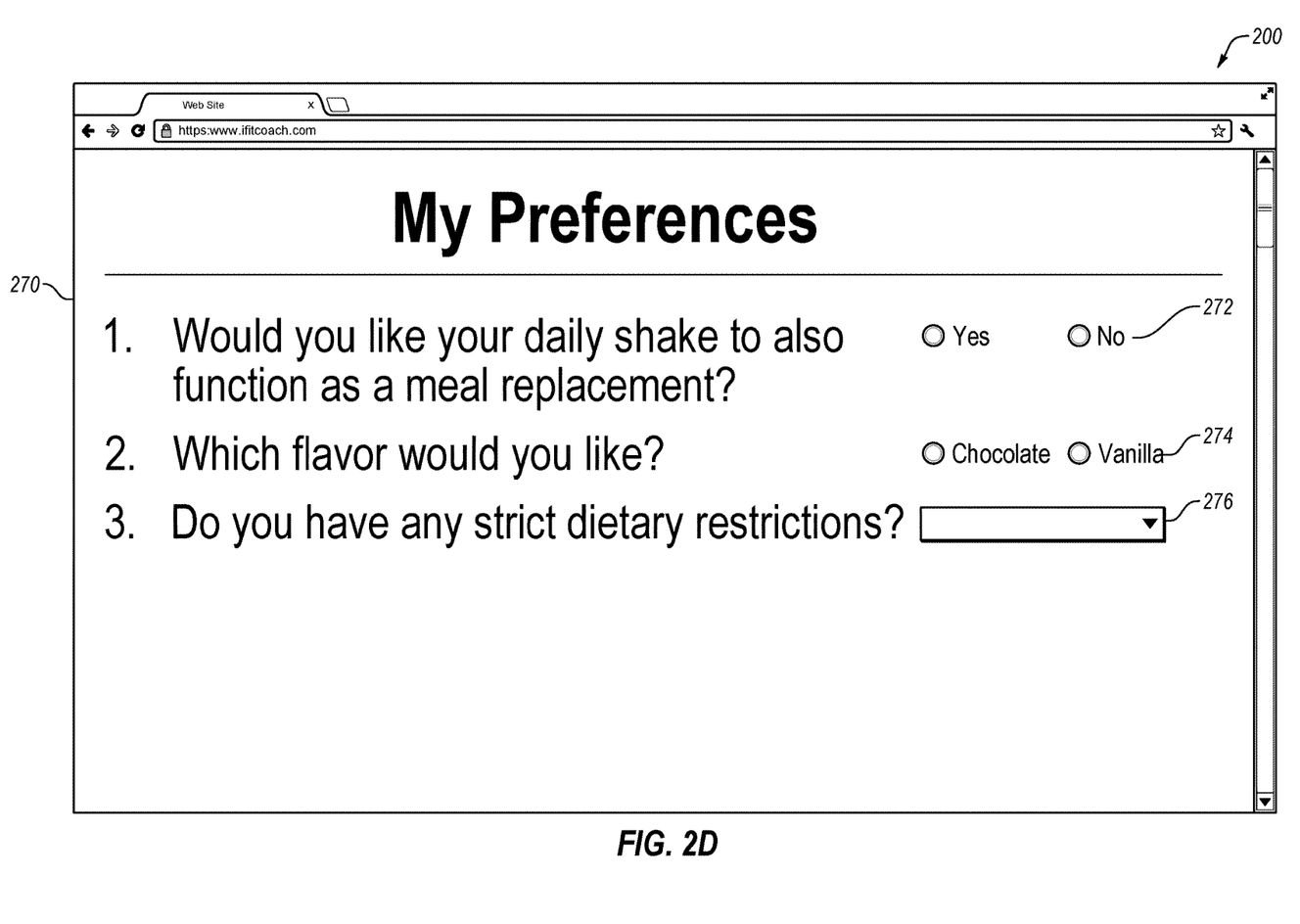

As disclosed in FIG. 2D, a fourth webpage 270 of the website 200 may be configured to be presented to a user in order to receive data regarding the preferences of the user. In particular, the fourth webpage 270 may be configured to receive the user's meal replacement goal, flavor preferences, and allergy status in data entry fields 272-276, respectively.

FIG. 3A-3D are a diagram of an example method 300 for customizing nutritional supplement recommendations. The method 300 may be performed, for example, by a software application being executed on the server 102, the laptop computer 104, the smartphone 106, the desktop computer 114, or the tablet 116, or some combination therefore, of FIG. 1. The method 300 may be employed to determine which of sixteen different nutritional supplement shakes a user should be recommended. These sixteen different nutritional supplement shakes include (1) a plant based meal replacement shake for males, (2) a plant based meal replacement shake for females, (3) a plant based protein shake for males, (4) a plant based protein shake for females, (5) a weight loss meal replacement shake for males, (6) a weight loss meal replacement shake for females, (7) a weight loss protein shake for males, (8) a weight loss protein shake for females, (9) a cardio meal replacement shake for males, (10) a cardio meal replacement shake for females, (11) a cardio protein shake for males, (12) a cardio protein shake for females, (13) a lean and tone meal replacement shake for males, (14) a lean and tone meal replacement shake for females, (15) a lean and tone protein shake for males, and (16) a lean and tone protein shake for females.

Figure 3A:
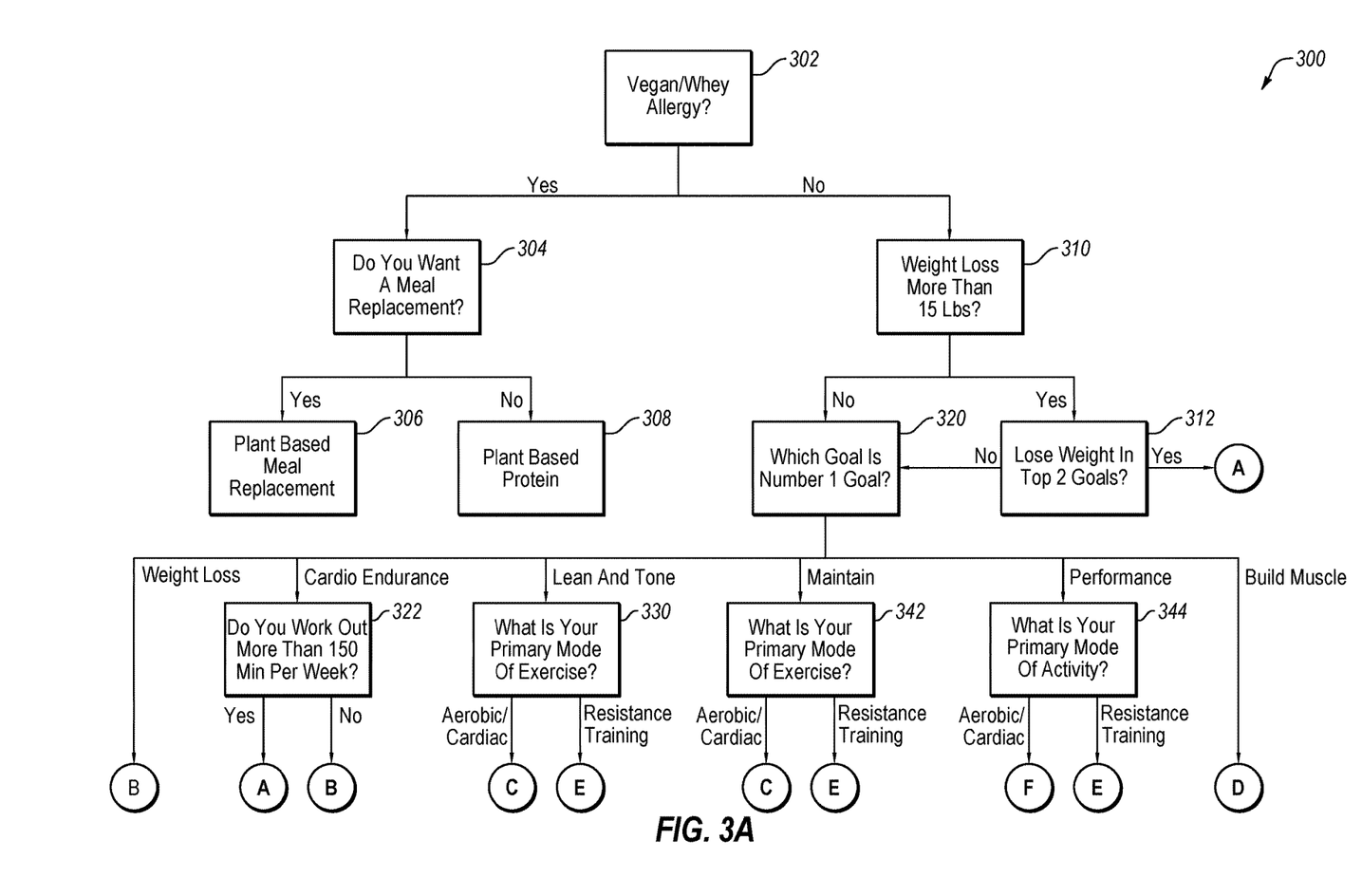
FIGS. 3A-3D are a diagram of an example method for customizing nutritional supplement recommendations.
Figure 3B:
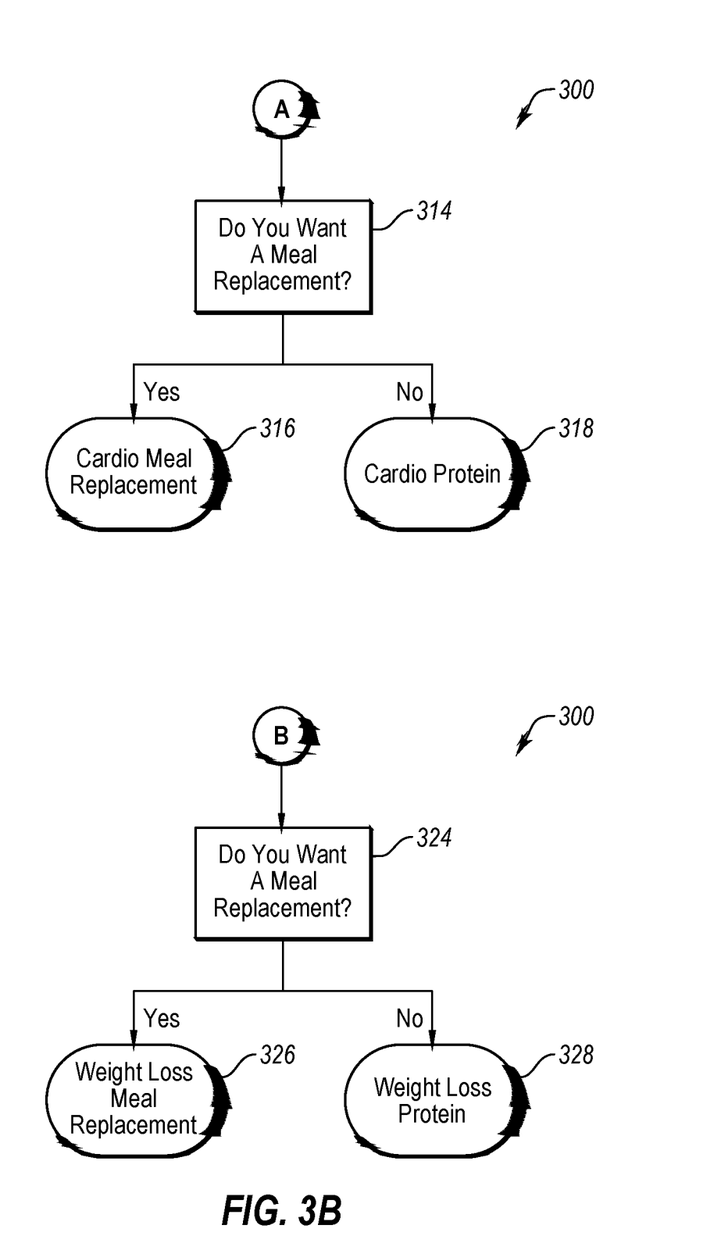
Figure 3C:
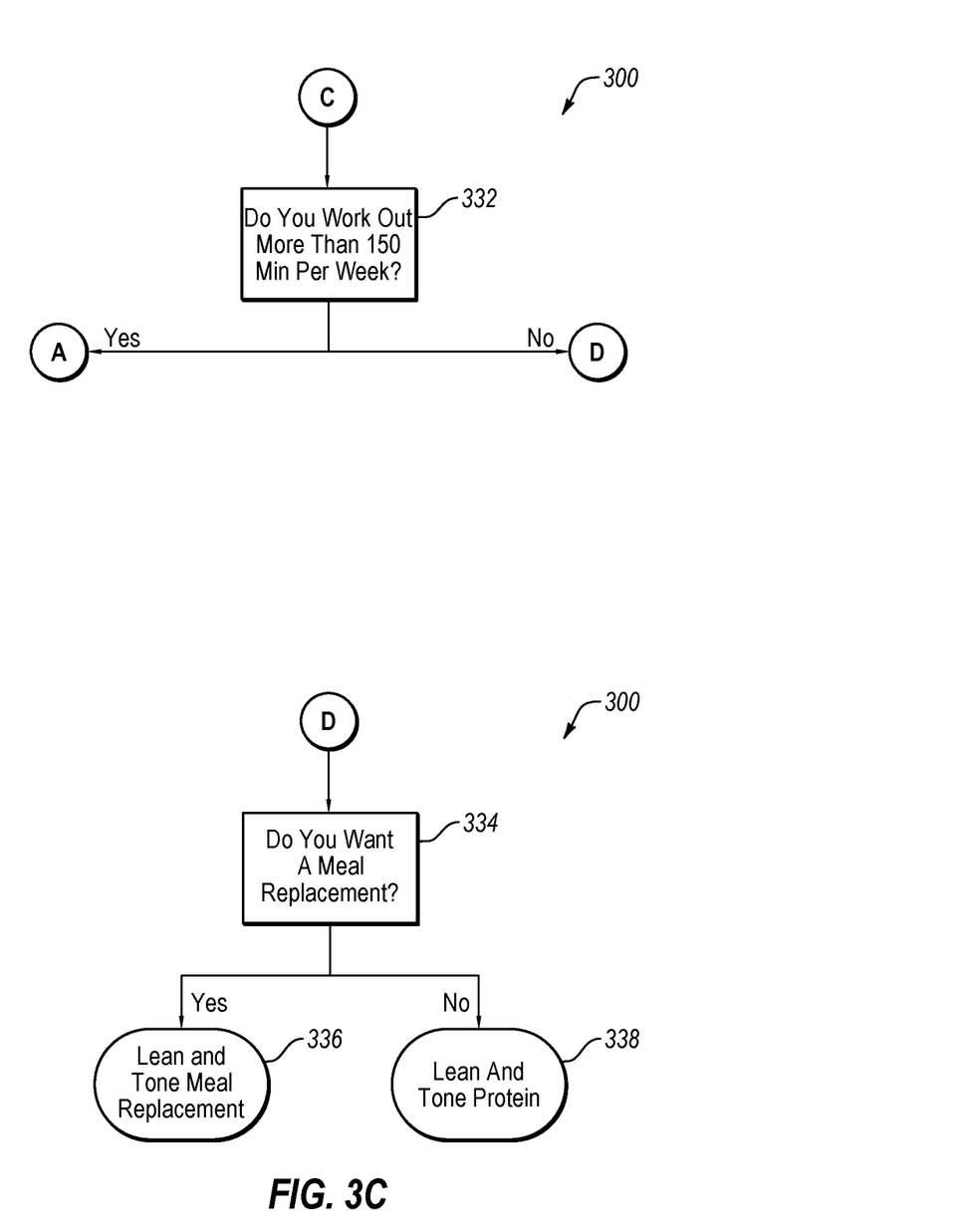
Figure 3D:
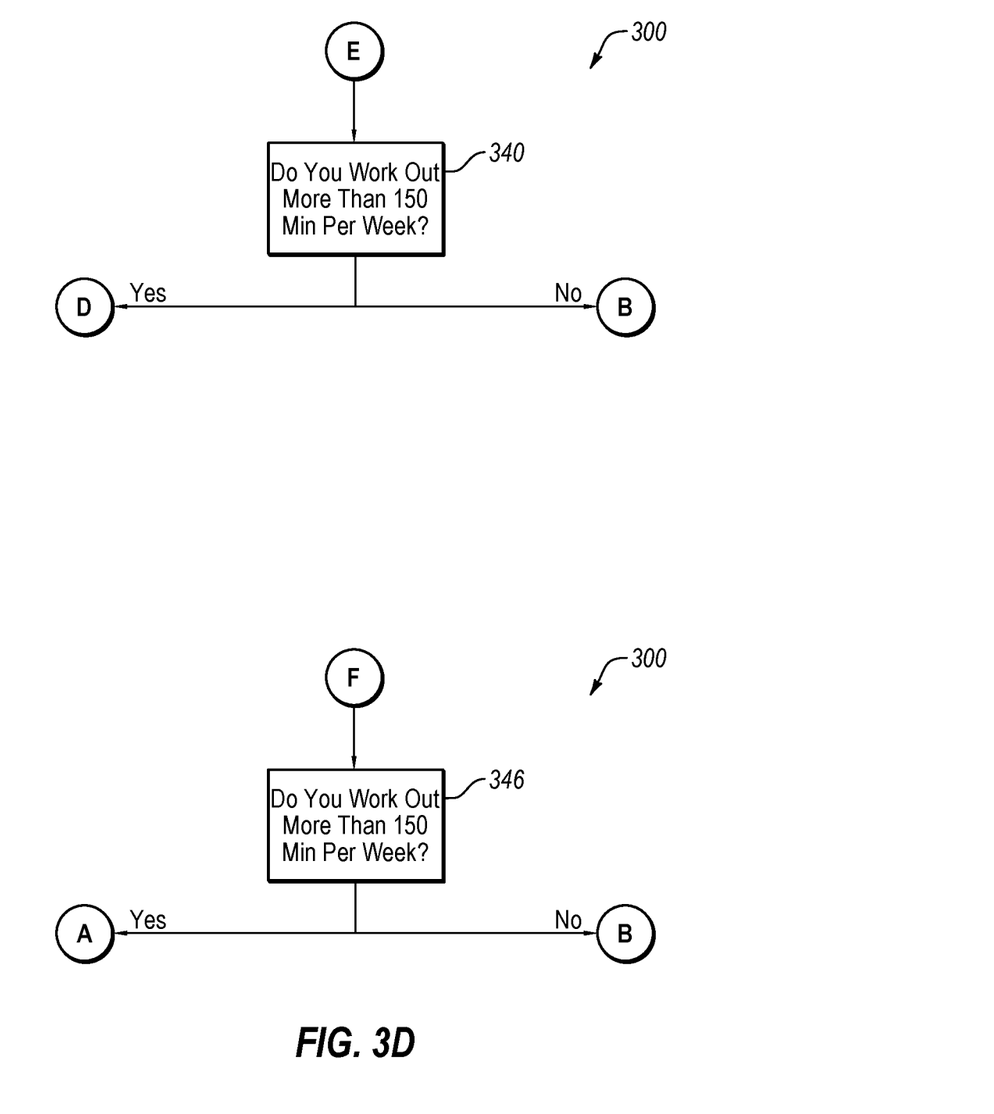

As disclosed in FIG. 3A, the method 300 first determines at 302 whether a user is a vegan or has a whey allergy. If so (Yes at 302), the method 300 determines at 304 whether the user wants a meal replacement. If so (Yes at 304), the method 300 determines at 306 that the user should be recommended either the male or female plant based meal replacement shake, depending on whether the user is male or female. If not (No at 304), the method 300 determines at 308 that the user should be recommended either the male or female plant based protein shake.

If the method 300 determines at 302 that the user is not vegan and does not have a whey allergy (No at 302), the method 300 determines at 310 whether the user has a goal to achieve a weight loss of more than 15 pounds. If so (Yes at 310), the method 300 determines at 312 whether a weight loss goal is ranked in the top two of the user's goals. If so (Yes at 312), the method 300 determines at 314, as disclosed in FIG. 3B, whether the user wants a meal replacement. If so (Yes at 314), the method 300 determines at 316 that the user should be recommended either the male or female cardio meal replacement shake. If not (No at 314), the method 300 determines at 318 that the user should be recommended either the male or female cardio protein shake.

As disclosed in FIG. 3A, if the method 300 determines at 312 that a weight loss goal is not ranked in the top two of the user's goals (No at 312), the method 300 determines at 320 which of the user's goals is ranked as the user's number one goal. If the user's number one goal is weight loss (Weight Loss at 320), the method 300 returns to 314, as discussed above.

As disclosed in FIG. 3A, if the method 300 determines at 320 that the user's number one goal is cardio endurance (Cardio Endurance at 320), the method 300 determines at 322 whether the user works out more than 150 minutes per week. If so (Yes at 322), the method 300 returns to 314, as discussed above. If not (No at 322), the method 300 determines at 324, as disclosed in FIG. 3B, whether the user wants a meal replacement. If so (Yes at 324), the method 300 determines at 326 that the user should be recommended either the male or female weight loss meal replacement shake. If not (No at 324), the method 300 determines at 328 that the user should be recommended either the male or female weight loss protein shake.

As disclosed in FIG. 3A, if the method 300 determines at 320 that the user's number one goal is lean and tone (Lean and Tone at 320), the method 300 determines at 330 the user's primary mode of exercise. If the user's primary mode of exercise is aerobic or cardiac (Aerobic/Cardiac at 330), the method determines at 332 whether the user works out more than 150 minutes per week. If so (Yes at 332), the method 300 returns to 314, as discussed above. If not (No at 332), the method 300 determines at 334 whether the user wants a meal replacement. If so (Yes at 334), the method 300 determines at 336 that the user should be recommended either the male or female lean and tone meal replacement shake. If not (No at 334), the method 300 determines at 338 that the user should be recommended either the male or female lean and tone protein shake. If the user's primary mode of exercise is resistance training (Resistance Training at 330), the method determines at 340 whether the user works out more than 150 minutes per week. If so (Yes at 340), the method 300 returns to 334, as discussed above. If not (No at 340), the method 300 returns to 324, as discussed above.

As disclosed in FIG. 3A, if the method 300 determines at 320 that the user's number one goal is maintaining a current fitness level (Maintain at 320), the method 300 determines at 342 the user's primary mode of exercise. If the user's primary mode of exercise is aerobic or cardiac (Aerobic/Cardiac at 342), the method returns to 332 as discussed above. If the user's primary mode of exercise is resistance training (Resistance Training at 342), the method returns to 340 as discussed above.

As disclosed in FIG. 3A, if the method 300 determines at 320 that the user's number one goal is performance (Performance at 320), the method 300 determines at 344 the user's primary mode of activity. If the user's primary mode of activity is aerobic or cardiac (Aerobic/Cardiac at 344), the method determines at 346 whether the user works out more than 150 minutes per week. If so (Yes at 346), the method 300 returns to 314, as discussed above. If not (No at 346), the method 300 returns to 324, as discussed above. If the user's primary mode of exercise is resistance training (Resistance Training at 344), the method returns to 340 as discussed above.

As disclosed in FIG. 3A, if the method 300 determines at 320 that the user's number one goal is to build muscle (Build Muscle at 320), the method 300 returns to 334 as discussed above.

Figure 4:
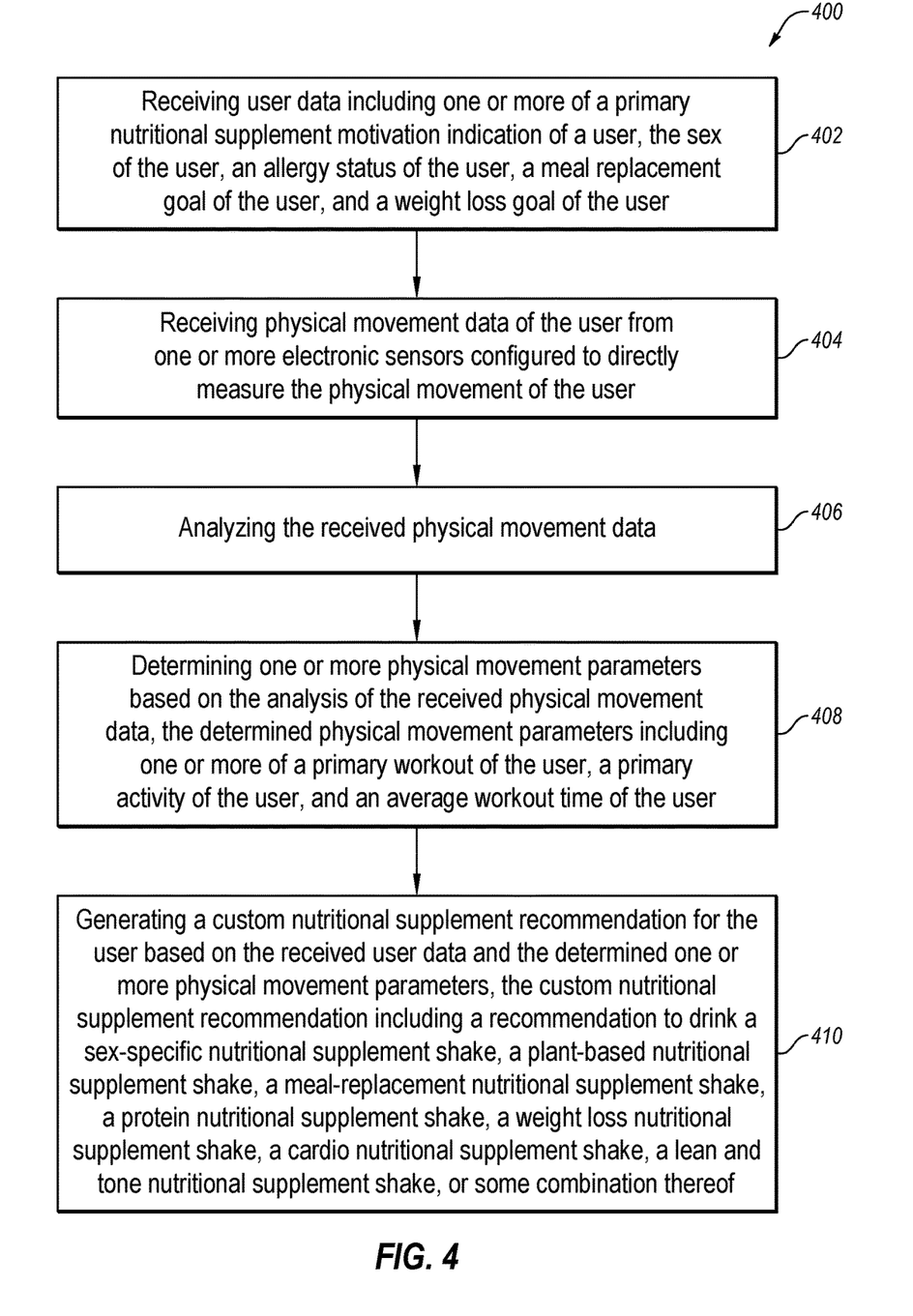
FIG. 4 is a diagram of another example method for customizing nutritional supplement recommendations.

FIG. 4 is a diagram of an example method 400 for customizing nutritional supplement recommendations. The method 400 may be performed, for example, by a software application being executed on the server 102, the laptop computer 104, the smartphone 106, the desktop computer 114, or the tablet 116, or some combination therefore, of FIG. 1.

The method 400 may include receiving, at 402, user data including one or more of a primary nutritional supplement motivation indication of a user, the sex of the user, an allergy status of the user, a meal replacement goal of the user, and a weight loss goal of the user.

The method 400 may include receiving, at 404, physical movement data of the user from one or more electronic sensors configured to directly measure physical movement of the user.

The method 400 may include analyzing, at 406, the received physical movement data.

The method 400 may include determining, at 408, one or more physical movement parameters based on the analysis of the physical movement data, the physical movement parameters including one or more of a primary workout of the user, a primary activity of the user, and an average workout time of the user.

The method 400 may include generating, at 410, a custom nutritional supplement recommendation for the user based on the received user data and the determined one or more physical movement parameters. The custom nutritional supplement recommendation may include a recommendation to drink a sex-specific nutritional supplement shake, a plant-based nutritional supplement shake, a meal-replacement nutritional supplement shake, a protein nutritional supplement shake, a weight loss nutritional supplement shake, a cardio nutritional supplement shake, a lean and tone nutritional supplement shake, or some combination thereof.

INDUSTRIAL APPLICABILITY

In general, the methods for customizing nutritional supplement recommendations disclosed above generate custom nutritional supplement recommendations for users based on various data that is received or determined. Various modifications to the methods disclosed above will now be disclosed.

The software application disclosed herein that is configured to receive data, analyze data, make determinations with respect to data, and generate custom nutritional supplement recommendations may be configured to be executed on one or more computing devices. For example, the computing devices may include, but are not limited to, an application or app that is executed on a smartphone, a smart watch, a smart panel of a smart home network, an exercise machine, a laptop computer, a tablet, or a desktop computer. Further, the software application may be distributed across two or more computing devices that communicate with each other over a wired or wireless network.

Further, the software application disclosed herein may include the use of a special-purpose or general-purpose computer, including various computer hardware or software. The software application may be implemented using non-transitory computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including RAM, ROM, EEPROM, CD-ROM or other optical disk storage, magnetic disk storage or other magnetic storage devices, or any other storage medium which may be used to carry or store one or more desired programs having program code in the form of computer-executable instructions or data structures and which may be accessed and executed by a general-purpose computer, special-purpose computer, or virtual computer such as a virtual machine. Combinations of the above may also be included within the scope of computer-readable media. Computer-executable instructions comprise, for example, instructions and data which, when executed by one or more processors, cause a general-purpose computer, special-purpose computer, or virtual computer such as a virtual machine to perform a certain method, function, or group of methods or functions.

The communication between computing devices disclosed herein may be accomplished over any wired or wireless communication network including, but not limited to, a Local Area Network (LAN), a Wide Area Network (WAN), a Wireless Application Protocol (WAP) network, a Bluetooth network, an ANT network, or an Internet Protocol (IP) network such as the Internet, or some combination thereof.

The receipt of data from a user disclosed herein in connection with various webpages of a website may additionally or alternatively be accomplished using other data gathering technologies including, but not limited to, receiving data from a user via data entry interfaces of an app on a smartphone or gathering data regarding a user by accessing databases that already store the desired data such as registration databases of an app server or a website server, or some combination thereof. Further, the receipt of data from a user disclosed herein in connection with various webpages of a website is example data only, and other types and specificity of data may additionally or alternatively be received from a user.

The sixteen different nutritional supplement shakes disclosed herein are just one example of a set of nutritional supplements that can be recommended to a user based on received and determined data. This set of nutritional supplements may be recommended using the methods disclosed herein. However, other sets of nutritional supplements may also be recommended using the method 300 or the method 400 or some combination thereof, and these methods are therefore not limited to use with the sixteen different nutritional supplement shakes disclosed herein.

The electronic sensors disclosed herein that are configured to directly measure the physical movement of the user may include both portable as well as stationary electronic sensors. Portable electronic sensors may include, but are not limited to, electronic sensors built into smart watches, fitness trackers, sport watches, head mounted displays, smart clothing, smart jewelry, vehicles, sports equipment, or implantables configured to be implanted in the human body, or some combination thereof. Stationary electronic sensors may include, but are not limited to, sensors built into exercise machines, furniture, beds or bedding (to measure physical movement while in bed and/or while asleep), flooring, walls, ceilings, doorways, or fixtures along paths and roadways, or some combination thereof. These sensors configured to measure the physical movement of the user may include, but are not limited to, sensors that measure physical movement using infrared, microwave, ultrasonic, tomographic, GPS, accelerometer, gyroscope, odometer, tilt, speedometer, piezoelectric, or video technologies, or some combination thereof.

The use of one or more electronic sensors in the example methods disclosed herein may solve the problem of a subjective recommendation from a dietitian that is based on subjective information provided by a user. In particular, since a dietitian is a human being, the dietitian is inherently biased and any recommendations are necessarily subjective instead of objective. Further, there are severe limitations to what types of information, and accuracy of information, that a human user can gather and convey to the human dietitian. The use of one or more electronic sensors in the example methods disclosed herein may solve these problems by using highly sophisticated and specialized electronic sensors that are configured to objectively and directly measure the physical movement of the user resulting in objective physical movement data and then sending that objective physical movement data to the objective software application disclosed herein instead of a subjective human dietitian. These electronic sensors may have specific tolerances and may enable a single computing device to measure multiple users in multiple remote locations. None of these capabilities are available to a human user absent these highly sophisticated and specialized electronic sensors. These highly sophisticated and specialized electronic sensors may therefore solve the problems with the prior art method by objectively and accurately measuring physical movement of the user instead of relying on subjective and biased observations of a user.

Further, the example methods disclosed herein are not directed to an abstract idea because they solve a technical problem using highly sophisticated and specialized electronic sensors. The data generated by these electronic sensors simply has no equivalent to pre-electronic sensor, manual paper-and-pencil data.

Also, the example methods disclosed herein may improve the technical field of automated nutritional supplement recommendations. For example, the technical field of automated nutritional supplement recommendations may be improved by the example methods disclosed herein at least because the prior art method did not enable the automatic measurement of the physical movement of a user and the automatic sending of physical movement data to a software application capable of customizing a nutritional supplement recommendation based on an automatic analysis and determination of parameters from the received physical movement data.

What is claimed is:

1. A method for customizing nutritional supplement shake recommendations, the method comprising:
   receiving, at a server, a primary nutritional supplement motivation indication of a user, entered on a webpage of a website hosted at the server;
   receiving, at the server, a secondary nutritional supplement motivation indication of the user, entered on the webpage of the website hosted at the server;
   receiving, at the server, a ranking by the user of the primary and secondary nutritional supplement motivation indications, entered on the webpage of the website hosted at the server;
   receiving, at the server, physical movement data of the user from one or more activity trackers having one or more electronic sensors configured to directly and automatically measure physical movement of the user and configured to wirelessly transmit the physical movement data to the server;
   analyzing, at the server, the physical movement data;
   determining, at the server, one or more physical movement parameters based on the analysis of the physical movement data; and
   generating, at the server, a custom nutritional supplement shake recommendation for the user based on the received primary nutritional supplement motivation indication, the received secondary nutritional supplement motivation indication of the user, the received ranking by the user of the primary and secondary nutritional supplement motivation indications, and the determined one or more physical movement parameters.

2. The method of claim 1, wherein the one or more activity trackers include a wearable activity tracker configured to be worn on a wrist of the user.

3. The method of claim 1, wherein the determined one or more physical movement parameters include a primary workout, or a primary activity, of the user.

4. The method of claim 1, wherein the determined one or more physical movement parameters include an average frequency of working out of the user and an average duration of each workout of the user.

5. The method of claim 1, wherein:
   the method further comprises receiving, at the server, the sex of the user entered on the webpage of the website hosted at the server; and
   the generating, at the server, of the custom nutritional supplement shake recommendation for the user is further based on the received sex of the user.

6. The method of claim 5, wherein the custom nutritional supplement shake recommendation includes a recommendation to drink a sex-specific nutritional supplement shake.

7. The method of claim 1, wherein:
   the method further comprises receiving, at the server, an allergy status of the user entered on the webpage of the website hosted at the server; and
   the generating, at the server, of the custom nutritional supplement shake recommendation for the user is further based on the received allergy status of the user.

8. The method of claim 7, wherein the custom nutritional supplement shake recommendation includes a recommendation to drink a plant-based nutritional supplement shake.

9. The method of claim 1, wherein:
   the method further comprises receiving, at the server, a meal replacement goal of the user entered on the webpage of the website hosted at the server; and
   the generating, at the server, of the custom nutritional supplement shake recommendation for the user is further based on the received meal replacement goal of the user.

10. The method of claim 9, wherein the custom nutritional supplement shake recommendation includes a recommendation to drink a meal-replacement nutritional supplement shake.

11. The method of claim 9, wherein the custom nutritional supplement shake recommendation includes a recommendation to drink a protein nutritional supplement shake.

12. The method of claim 1, wherein:
   the method further comprises receiving, at the server, a weight loss goal of the user entered on the webpage of the website hosted at the server; and
   the generating, at the server, of the custom nutritional supplement shake recommendation for the user is further based on the received weight loss goal of the user.

13. The method of claim 12, wherein the custom nutritional supplement shake recommendation includes a recommendation to drink a weight loss nutritional supplement shake.

14. The method of claim 1, wherein the custom nutritional supplement shake recommendation includes a recommendation to drink a cardio nutritional supplement shake.

15. The method of claim 1, wherein the custom nutritional supplement shake recommendation includes a recommendation to drink a lean and tone nutritional supplement shake.

16. One or more non-transitory computer-readable media storing one or more programs that are configured, when executed, to cause one or more processors of a server to perform a method for customizing nutritional supplement shake recommendations, the method comprising:
   receiving, at the server, a primary nutritional supplement motivation indication of a user entered on a webpage of a website hosted at the server;

receiving, at the server, a secondary nutritional supplement motivation indication of the user entered on the webpage of the website hosted at the server;

receiving, at the server, a ranking by the user of the primary and secondary nutritional supplement motivation indications entered on the webpage of the website hosted at the server;

receiving, at the server, physical movement data of the user from one or more activity trackers having one or more electronic sensors configured to directly and automatically measure physical movement of the user and configured to wirelessly transmit the physical movement data to the server;

analyzing, at the server, the received physical movement data;

determining, at the server, one or more physical movement parameters based on the analysis of the received physical movement data; and generating, at the server, a custom nutritional supplement shake recommendation for the user based on the received primary nutritional supplement motivation indication, the received secondary nutritional supplement motivation indication of the user, the received ranking by the user of the primary and secondary nutritional supplement motivation indications, and the determined one or more physical movement parameters.

17. The one or more non-transitory computer-readable media of claim 16, wherein:

the one or more activity trackers include a wearable activity tracker configured to be worn on a wrist of the user; and the determined one or more physical movement parameters include a primary workout of the user, a primary activity of the user, and an average workout time of the user.

18. The one or more non-transitory computer-readable media of claim 16, wherein:

the method further comprises receiving, at the server, the sex of the user, an allergy status of the user, a meal replacement goal of the user, and a weight loss goal of the user, entered on the webpage of the website hosted at the server; and the generating, at the server, of the custom nutritional supplement shake recommendation for the user is further based on the received sex of the user, the received allergy status of the user, the received meal replacement goal of the user, and the received weight loss goal of the user.

19. The one or more non-transitory computer-readable media of claim 16, wherein:

the custom nutritional supplement shake recommendation includes a recommendation to drink a sex-specific nutritional supplement shake, a plant-based nutritional supplement shake, a meal-replacement nutritional supplement shake, a protein nutritional supplement shake, a weight loss nutritional supplement shake, a cardio nutritional supplement shake, or a lean and tone nutritional supplement shake, or some combination thereof.

20. A method for customizing nutritional supplement shake recommendations, the method comprising:

receiving, at a server, user data including a primary nutritional supplement motivation indication of a user, a secondary nutritional supplement motivation indication of the user, a ranking by the user of the primary and secondary nutritional supplement motivation indications, a birthday of the user, a height of the user, the sex of the user, a current weight of the user, an allergy status of the user, a cardio training indication of the user, a resistance training indication of the user, a flavor preference of the user, an average frequency of working out of the user, an average duration of each workout of the user, and a weight loss goal weight of the user, entered on a webpage of a website hosted at the server;

receiving, at the server, a ranking of the primary and secondary nutritional supplement motivation indications entered on the webpage of the website hosted at the server;

receiving, at the server, physical movement data of the user from one or more activity trackers having one or more electronic sensors configured to directly and automatically measure physical movement of the user and configured to wirelessly transmit the physical movement data to the server;

analyzing, at the server, the received physical movement data;

determining, at the server, one or more physical movement parameters based on the analysis of the received physical movement data; and generating, at the server, a custom nutritional supplement shake recommendation for the user based on the received user data and the determined one or more physical movement parameters.

* * * * *